(12) United States Patent
Dickson et al.

(10) Patent No.: US 8,632,540 B2
(45) Date of Patent: Jan. 21, 2014

(54) SURGICAL INSTRUMENT FOR TISSUE REMOVAL

(71) Applicants: Clark B. Dickson, Grosse Pointe Farms, MI (US); Gene P. Parunak, Saline, MI (US)

(72) Inventors: Clark B. Dickson, Grosse Pointe Farms, MI (US); Gene P. Parunak, Saline, MI (US)

(73) Assignee: ENT Biotech Solutions, LLC, Grosse Pointe Farms, MI (US)

( * ) Notice: Subject to any disclaimer, the term of this patent is extended or adjusted under 35 U.S.C. 154(b) by 0 days.

(21) Appl. No.: 13/660,552

(22) Filed: Oct. 25, 2012

(65) Prior Publication Data

US 2013/0274740 A1 Oct. 17, 2013

Related U.S. Application Data

(60) Provisional application No. 61/622,658, filed on Apr. 11, 2012, provisional application No. 61/683,648, filed on Aug. 15, 2012.

(51) Int. Cl.
*A61B 18/14* (2006.01)

(52) U.S. Cl.
USPC ............................................. 606/52; 606/207

(58) Field of Classification Search
USPC ............. 606/37, 39, 40, 48, 50–52, 207, 206, 606/208
See application file for complete search history.

(56) References Cited

U.S. PATENT DOCUMENTS

| | | | |
|---|---|---|---|
| 4,300,564 A * | 11/1981 | Furihata | 606/127 |
| 5,603,711 A * | 2/1997 | Parins et al. | 606/51 |
| 5,603,712 A | 2/1997 | Koranda et al. | |
| 5,833,703 A | 11/1998 | Manushakian | |
| 6,024,744 A | 2/2000 | Kese et al. | |
| 6,277,117 B1 | 8/2001 | Tetzlaff et al. | |
| 6,312,430 B1 | 11/2001 | Wilson et al. | |
| 6,358,249 B1 | 3/2002 | Chen et al. | |
| 6,371,956 B1 | 4/2002 | Wilson et al. | |
| 6,511,480 B1 | 1/2003 | Tetzlaff et al. | |
| 7,179,254 B2 * | 2/2007 | Pendekanti et al. | 606/28 |
| 2003/0109875 A1 | 6/2003 | Tetzlaff et al. | |
| 2006/0025766 A1 | 2/2006 | Heinrich et al. | |
| 2009/0043304 A1 | 2/2009 | Tetzlaff et al. | |

(Continued)

FOREIGN PATENT DOCUMENTS

| | | |
|---|---|---|
| JP | 2009148575 A | 7/2009 |
| KR | 2002047144 A | 6/2002 |

OTHER PUBLICATIONS

International Search Report of PCT/US2013/036253, Corrected Version Mailed on Aug. 14, 2013, 6 pages.

*Primary Examiner* — Michael Peffley
*Assistant Examiner* — Thomas Giuliani
(74) *Attorney, Agent, or Firm* — Brinks Gilson & Lione

(57) ABSTRACT

An electrosurgical instrument for removal of tissue from a patient. The electrosurgical instrument includes a handle portion having a pair of end effectors configured to remove tissue, connected to and supported by the handle portion for relative movement generally toward one another. One of the end effectors includes a conductive cutting portion that is configured to receive electrical energy from an electrical energy source. The other of the end effectors includes an opposing portion. The opposing portion is brought into a position generally opposing the conductive cutting portion during relative movement of the end effectors toward one another. When electrical energy is conducted through the conductive cutting portion, removal and cauterization of the tissue from the patient is facilitated.

24 Claims, 8 Drawing Sheets

(56) References Cited

U.S. PATENT DOCUMENTS

| | | | |
|---|---|---|---|
| 2009/0254081 A1* | 10/2009 | Allison et al. | 606/39 |
| 2009/0306660 A1* | 12/2009 | Johnson et al. | 606/51 |
| 2009/0326530 A1* | 12/2009 | Orban et al. | 606/51 |
| 2010/0121321 A1 | 5/2010 | Ryan | |

\* cited by examiner

SURGICAL INSTRUMENT FOR TISSUE REMOVAL

CROSS REFERENCE TO RELATED APPLICATIONS

This application is a nonprovisional application that claims priority to U.S. Provisional Application No. 61/622,658, filed on Apr. 11, 2012, and to U.S. Provisional Application No. 61/683,648 filed on Aug. 15, 2012, the entire contents of both of which are hereby incorporated by reference.

BACKGROUND OF THE INVENTION

1. Field of the Invention

The present invention generally relates to a surgical instrument for tissue removal. More specifically, the present invention relates to a surgical instrument for performing the removal of either palatine and pharyngeal types of tonsils, and even more particularly, the latter type of tonsils, which is commonly referred to as adenoids.

2. Description of Related Technology

As seen in FIG. 1, tonsils (T) and adenoids (A) are a masses of lymphoid tissue generally found in the oral and nasal cavities ($C_o$, $C_n$) respectively. The tonsils are a set of tissue located on both sides at the back of the throat. Adenoids, on the other hand, comprise a single clump of tissue that is not directly visible from outside the mouth. The adenoids are located rearward of the nasal cavity and above the soft palate, generally where the nasal cavity merges with the throat.

Both tonsils and adenoids are subject to infection, particularly in children. When infected, the enlarged tissue may impair breathing through the nose, cause snoring, cause retention of fluid (and, therefore, infection of the ears (caused by the adenoids)), cause accumulation of nasal secretions (and, therefore, sinus infections (caused by the adenoids), and cause difficulty in swallowing and breathing (caused by the tonsils). Since neither tissue has been observed to serve an immunological or other function in adulthood, when infections are common and recurring, one preferred treatment is the surgical removal of the tissue, which is called either an adenoidectomy or a tonsillectomy.

Common methods for removing the adenoids and tonsils include utilization of a curette, forceps or an electrocautery device. A curette is a surgical instrument having a spoon or otherwise shaped end that is used to scrape and remove the desired tissue. With an electrocautery device, radio-frequency energy is applied to tissue, heating the water in the local tissues, thereby weakening the tissue, allowing mechanical scraping removal and simultaneous cauterizing of removal site to reduce or stop bleeding.

Of the two procedures, some physicians prefer electrocautery since it minimizes the bleeding associated with removal of the tissue. However, current instruments for electrocautery are not specifically designed for rapid removal of either the tonsils or the adenoids.

SUMMARY

In view of the above limitations and drawbacks, in one aspect, an electrosurgical instrument for removal of tissue from a patient is provided, the electrosurgical instrument comprising: a handle portion; a pair of end effectors configured to remove tissue, the end effectors being connected to and supported by the handle portion for relative movement generally toward one another; one of the end effectors including a conductive cutting portion, the conductive cutting portion being configured to receive electrical energy from an electrical energy source; the other of the end effectors including an opposing portion, the opposing portion being brought into a position generally opposing the conductive cutting portion during relative movement of the end effectors toward one another; and wherein when electrical energy is conducted through the conductive cutting portion facilitating removal and cauterization of the tissue from the patient.

In another aspect, the opposing portion is non-conductive, the electrosurgical instrument being a unipolar electrosurgical instrument.

In a further aspect, the end effector includes a curved arm portion and a tip, the conductive cutting portion being provided along at least a portion of the tip.

In an additional aspect, the tip portion is enlarged relative to the arm portion.

In still another aspect, the tip portion is ovoid or ring shape.

In yet a further aspect, at least part of the handle portion is electrically conductive and configured to electrically connect the end effector to the electrical energy source.

In an additional aspect, the opposing portion is conductive and configured to be electrically coupled to the electrical energy source, the electrosurgical instrument being a bi-polar electrosurgical instrument.

In another aspect, the conductive cutting portion and the opposing portion are opposite one another so as to bear against each other when brought fully together.

In still a further aspect, the conductive cutting portion and the opposing portion have complementary shapes to one another.

In yet an additional aspect, the end effectors are removably connected to the handle portion.

In another aspect, the end effectors are fixedly connected to the handle portion.

In an additional aspect, the handle portion is connected to the end effectors by pivotably connected lever members providing the electrosurgical instrument with a scissors construction.

In still another aspect, one of the lever members is electrically conductive and electrically connected to the conductive cutting portion.

In a further aspect, the conductive cutting portion includes a blade having a sharpened edge.

In another aspect, the conductive cutting portion further defines an exposed width portion, the exposed width portion extending in a direction away from the sharpened edge.

In an additional aspect, the opposing portion defines an edge cooperates with the conductive cutting portion to facilitate removal of tissue.

In yet a further aspect, at least part of the electrosurgical instrument is disposable.

In another aspect, the end effectors further include generally opposing clamping portions, the clamping portions being configured to clamp and secure dissected tissue.

In a further aspect, the clamping portions are adjacent to the conductive cutting portion and the opposing portion.

In an additional aspect, an electrosurgical instrument for removal of tissue from a patient is provided, the electrosurgical instrument comprising: a pair of opposing end effectors, at least one of the end effectors including a exposed electrode, at least one of the end effectors including a cutting portion and the other of the end effectors including an opposing portion opposing the cutting portion, each of the end effectors including opposed tissue retention portions; a handle coupled to the end effectors; an actuator associated with the handle and configured to cause relative movement of the end effectors toward each other whereby the tissue is constrained between the tissue retention portions, the opposing portion and the cutting portion being configured to engage tissue constrained between the tissue retention portions; the electrode being directly or indirectly electrically connected to a source of electrosurgical energy; and whereby when the tissue is constrained between the tissue retention portions and electrosurgical energy is applied to the electrode, at least a portion of the tissue is dissected by the cutting and opposing portions, cauterized by the electrode and held between the tissue retention portions for removal after being dissected.

In still another aspect, the end effectors are removably or fixedly connected to the handle.

In yet a further aspect, the conductive portion is unitarily formed with the cutting portion.

In an additional aspect, the cutting portion and opposing portion define congruent surfaces.

In yet another aspect, the congruent surfaces are aligned with each other when the cutting portion and opposing portion are moved toward each other by the actuator.

In a further aspect, a method of removing tissue from a patient utilizing an electrosurgical instrument is provided, the method comprising: providing an electrosurgical instrument having a pair of opposing end effectors, at least one of the end effectors including a conductive cutting portion and the other of the end effectors including an opposing portion, the end effectors each further including opposing tissue retention portions; positioning the conductive cutting portion on one lateral side of the tissue to be removed and positioning the opposing portion on an opposing lateral side of the tissue to be removed; positioning the tissue retention portions of each end effector on opposing lateral sides of the tissue to be removed; causing relative movement of the end effectors toward each other; constraining the tissue to be removed between the tissue retention portions; providing electrosurgical energy to the conductive cutting portion; passing electrosurgical energy through the tissue to be removed; dissecting the tissue through a combination of the electrosurgical energy passing through the tissue and the conducting cutting portion; cauterizing the tissue through a combination of the electrosurgical energy passing through the tissue and the conducting cutting portion; performing the dissecting and cauterizing steps while continuing to constrain the tissue between the tissue retention portions; and removing the dissected tissue from the patient while continuing to constrain the tissue between the tissue retention portions.

In still an additional aspect, the step of dissecting the tissue utilizes a sharpened edge formed on the conducting cutting portion.

In another aspect, the step of cauterizing the tissue utilizes a width of the conductive cutting portion extending in a direction away from the sharpened edge.

In a further aspect, the step of contacting an electrode with the patient at a location remote from the site of the tissue to be removed.

In yet an additional aspect, the positioning steps position tonsil tissue between the end effectors.

In another aspect, the tonsil tissue is pharyngeal tonsil tissue.

Further objects, features and advantages of this invention will become readily apparent to persons skilled in the art after a review of the following description, with reference to the drawings and claims that are appended to and form a part of this specification.

DETAILED DESCRIPTION

Figure 1:
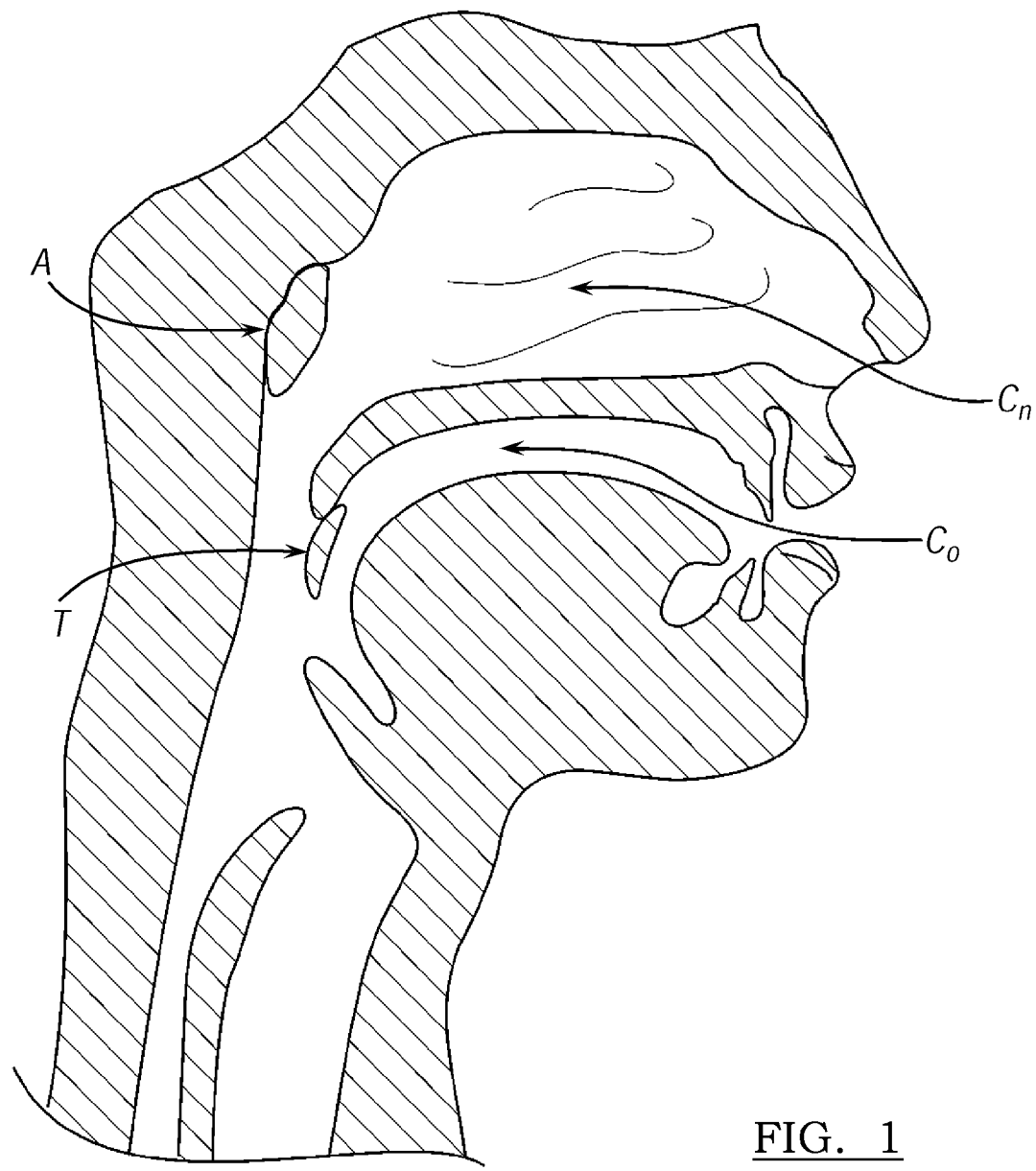
FIG. 1 is a diagrammatic illustration of the oral and nasal cavities of a person showing the relative locations of the tonsils and adenoids therein.
Figure 2A:
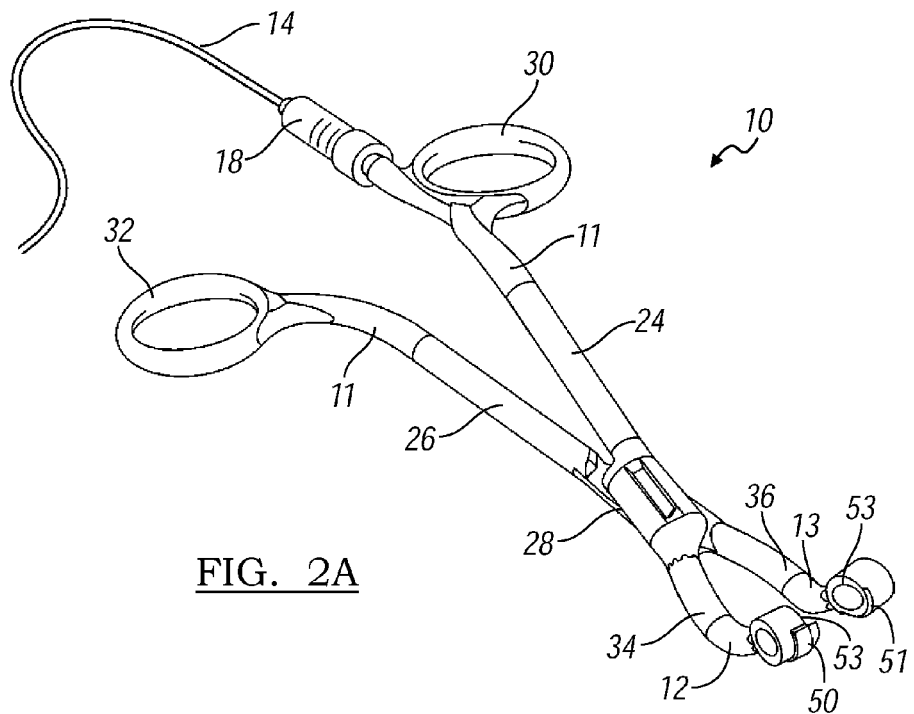
FIGS. 2a-2c are perspective views of cautery forceps embodying the principles of the present invention.
Figure 2B:
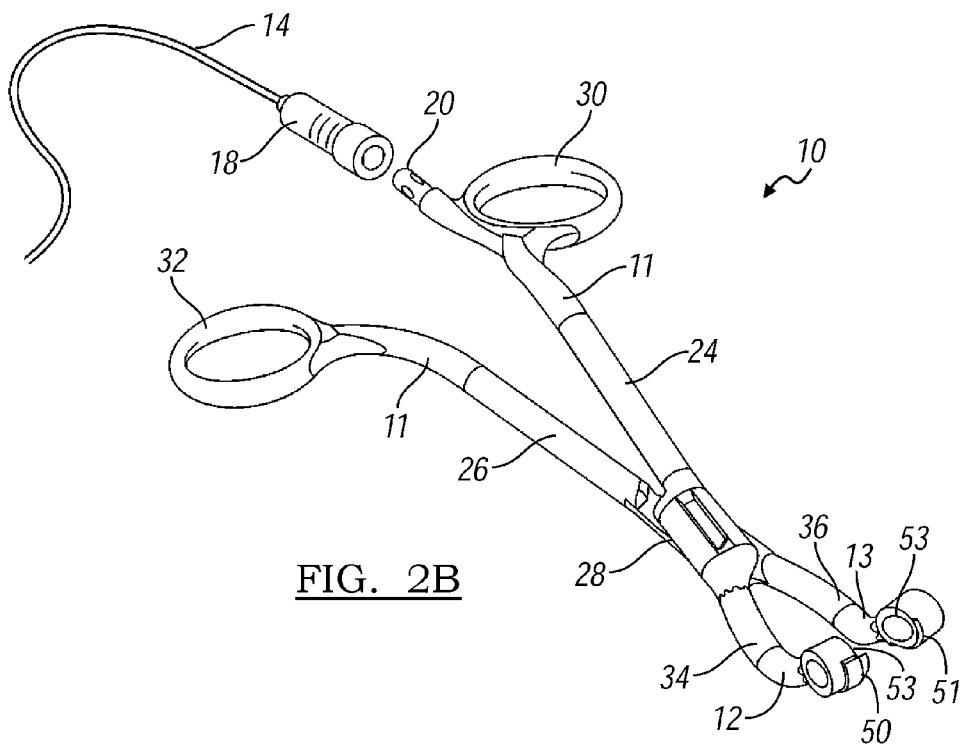
Figure 2C:
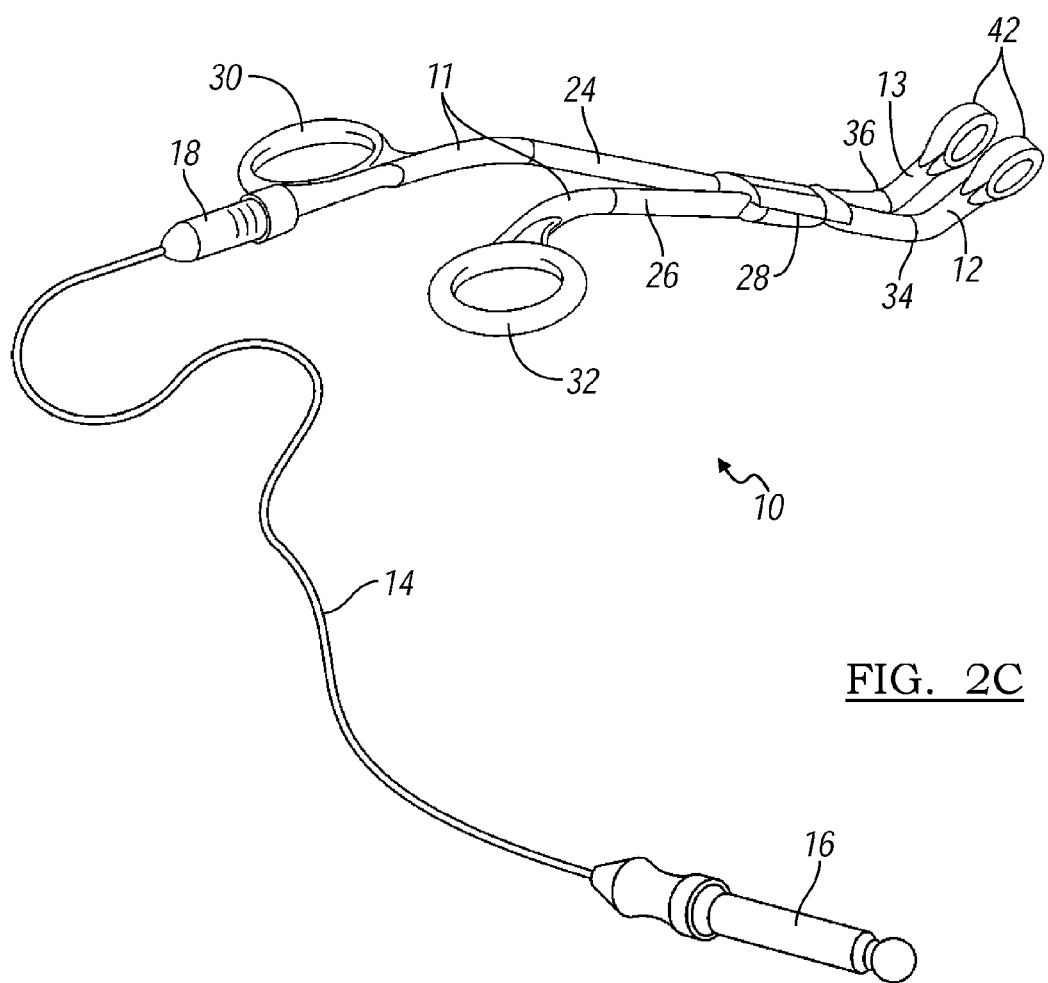

The present invention provides an electrosurgical instrument for removal of tissue. While those skilled in the art will appreciate that instruments incorporating the principles of the present invention are suitable for use in removing multiple types of tissue, described herein are instruments for removal of tonsil tissue, such as the palatine tonsils (commonly referred to as just the "tonsils") and, more particularly, pharyngeal tonsils (commonly referred to as the "adenoids"). For simplicity, the discussion that follows simply refers to the removal of the adenoids.

Overview

Referring now to FIGS. 2a-2c and 3, illustrated therein, and designated at 10, is an electrosurgical instrument in accordance with the principles of the present invention. As seen in these figures, the electrosurgical instrument 10 may generally be described as being in the shape of a pair of forceps. Unlike common forceps, however, the surgical instrument 10, hereinafter referred to as cautery forceps 10, includes a pair of handles 11 to which are mounted a pair of removable end effectors 12, 13. Additionally, the cautery forceps 10 include a means 14, such as a power cord, by which at least one of the end effectors 12, 13 can be connected to a suitable electrical power source.

Power Source

Preferably, the power source is an available source of power located in the room where the cautery forceps 10 are to be used. As such, the power source includes the required componentry needed to provide the proper voltage, current and frequency for electrocautery surgery. Generally, electrocautery requires a frequency in the radio frequency range, above 100 KHz and up to 5 MHz. This power source itself can be provided as an integrated system such that the power cable 14 is merely plugged into an outlet (not show) in the room. Alternately, the power source can be provided as a stand-alone power system located in the operating room or as a battery incorporated into the electrosurgical instrument.

Unipolar and Bipolar

The cautery forceps 10 according to the present invention are preferably unipolar (also known as monopolar) in their construction. In such a construction, the cautery forceps 10 themselves include a single electrode in one of the end effectors 12, which is further discussed below. During use, current flows from the electrode, through the patient, and to a return electrode affixed elsewhere on the patient's body.

In an alternative embodiment, the cautery forceps 10 are of a bipolar construction. In a bipolar construction, a second electrode is provided on the other end effector 13. During use of the bipolar cautery forceps 10, electrical current passes primarily from one electrode on one end effector to the second electrode on the other end effector. The current thus passes primarily through a localized portion of the affected tissue of the patient, which is located between the electrodes, and in contrast to flowing through the body of the patient to a remotely located electrode in the unipolar construction.

Handles

The handles 13 of the cautery forceps 10 in the illustrated embodiment are provided in conjunction with two lever members 24, 26 that are arranged such that the cautery forceps 10 operate in a traditional, scissors-like construction. In such a construction, the two lever members 24, 26 cross one another at a central pivot joint 28, which includes pivot axle. The handles 11 may be provided with finger rings or grips 30, 32 at one end, while the lever members 24, 26 terminate in mounting tips 34, 36 at the opposing end. By bringing the finger grips 30, 32 together, the opposing mounting tips 34, 36 are likewise brought toward one another.

Preferably, the lever members 24, 26 are solidly constructed of a metal material, such as surgical grade stainless steel, aluminum or another conductive material. Constructed in this manner, at least one of the lever members 24, 26 can operate as a conductor to transmit current through the cautery forceps 10, as further discussed below. The pivot joint 28 between the two lever members 24, 26 is constructed such that the two members 24, 26 are electrically isolated from one another by way of an insulating bushing (not shown) or other feature. Failure to electrically isolate the two lever members 24, 26 would result in the shorting of the electrical circuit and would render the end effectors 12, 13, which are themselves further discussed below, as inoperative in certain respects.

The finger rings 30, 32 of the handles 11 may be formed as a traditional ringed portion so as to facilitate the grasping of the cautery forceps 10 and the manipulation thereof by the surgeon. Alternatively, they may be provided with other shapes.

The lever members 24, 26 are electrically isolated from the surgeon by covering the lever members 24, 26 with an insulative material. Various means by which the lever members 24, 26 may be covered are envisioned and include dip coating or spray coating with rubber or plastisol or overmolding of the lever members 24, 26 with a polymer material, such as polycarbonate, ABS, HDPE, acrylic, or other material having the appropriate insulative characteristics. The material covering the lever members 24, 26 should also facilitate grasping of the handles 22 and minimize potential slipping of the cautery forceps 10 when held and in use by the surgeon.

The previously mentioned power cable 14 is configured at one end with an electrical connector 16, suitable for making the required electrical connection with the electrical power source. The opposing end of the power cable 14 is also provided with an electrical connector 18. This latter electrical connected 18 matingly engages a receptacle terminal 20 associated with one of the lever members 24 of the handles 11. As such, the connectors 16, 18 on each end of the power cable 14 are preferably one of a plug or receptacle terminal, such as a banana-plug or a multiple pronged RF surgical plug, suitable for a robust connection and electrical power supply.

In the illustrated embodiment, the terminal 20 is formed adjacent to the hand grip 30 of the lever member 24. While the terminal 20 is illustrated as being located adjacent to the ring portion of the hand grip 30, generally on the inward side thereof, it will be understood that the terminal 20 could be located elsewhere on the hand grip 30 or the lever member 24. Additionally, the terminal 22 may alternatively be attached to the lever member 24 via a suitable connection or it may be insert molded during the formation of the lever member 24.

End Effectors

Figure 5:
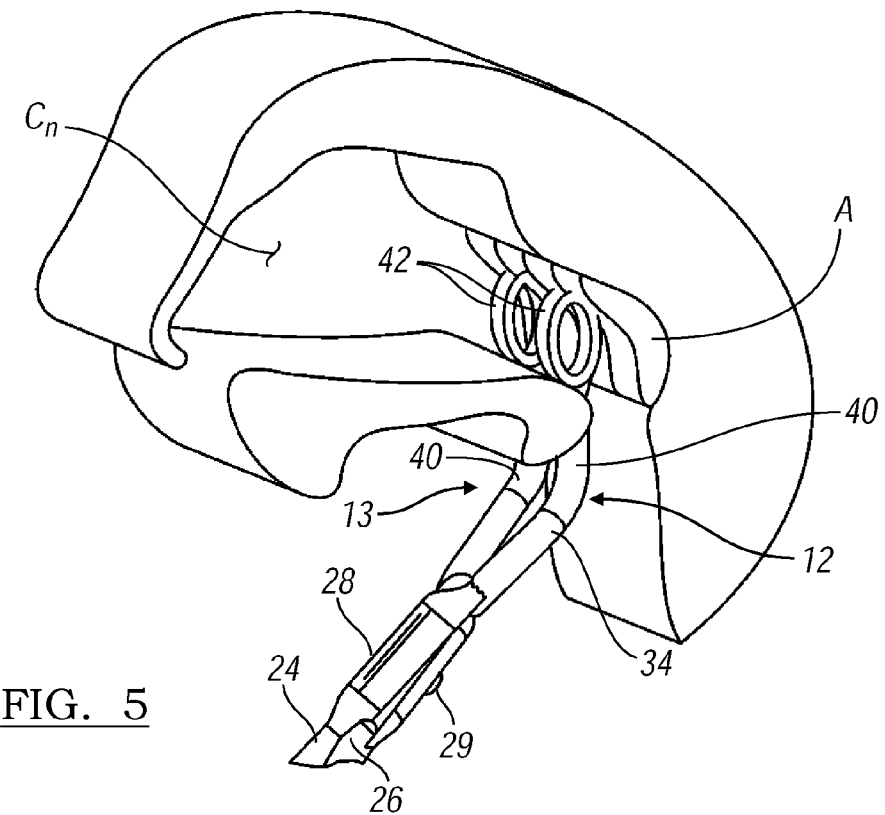
FIG. 5 is a diagrammatic illustration of the end effectors of the cautery forceps positioned at the interface of the oral and nasal cavities and adjacent to the soft palate and adenoids as may be positioned during use.

The end effectors 12, 13 are seen in FIGS. 2a-5 and each has the same general construction, being principally composed of an arm portion 40 and a tip portion 42, with the tip portion 42 being formed at a distal end of the arm portion 40. The arm portion 40 is curved along its length and the tip portion 42 is formed generally in an ovoid ring shape. The curvature and length of the arm portion 40 is such that it facilitates the positioning of the tip portion 42 in the vicinity of the adenoids, as seen in FIG. 5, so as to enhance the ease with which the adenoids are accessed and the ease with which the cautery forceps 10 are manipulated during the surgical procedure. The length and curvature of the arm portions 40 may be provided in a variety of configurations, including having straight portions, so as to accommodate differing patient anatomies and the preferences of the surgeons. Generally, however, the curvature of the arm portions 40 is such that during use and entry into the patient's oral cavity, the curvature of the arm portions 40 is directed upward toward at least the ends of the arm portions 40.

The end effectors 12, 13, and particularly the arm portions 40, may be rigid or may be bendable. If bendable, they should only be bendable to such a degree to allow the surgeon some amount of adjustability to accommodate variations in patient anatomy. They should not be so bendable that they undergo bending during use by the surgeon.

The oval ring shape of the tip portions 42 of the end effectors 12, 13 is enlarged relative to the arm portions 40 and assists in the removal of the adenoids. On one side of the ring shape, which is the inward, lower side seen in FIGS. 2a-3, the tip portions 42 are provided with cutting portions 50, 51. The other side of the ring shape, the inward upper side in FIGS. 2a-3, griping portions 53 are provided, which function as a mechanism by which the end effectors can grasp the tissue that is being cut and cauterized. This grasping of the tissue by the end effectors 12, 13 also efficiently allows for the removal of the cut tissue from the procedure site. While shown with an ovoid ring shape, the tip portions 42 of the end effectors 12, 13 may have alternative shapes, such as a recti-linear, a curvi-linear or other shapes.

Like the arm portions, the length and width of the ovoid ring shapes of the tip portions 42 may vary. By varying the shape of the tip portions 42, a variety of sized and shaped end effectors 12, 13 can be provided in kit form, allowing a surgeon to readily select, during the procedure, the end effector 12, 13 with a configuration that works best with a particular patient's anatomy.

The end effectors 12, 13 do, however, differ in one regard. Specifically, one end effector 12 includes a conductive insert 44 that extends through the arm and tip portions 40, 42 and operates as an electrode for cautery purposes. In one embodiment, the other end effector 13 may be formed with an insert 45 that is similar, but does not operate as the electrode. In another embodiment, the other end effector 13 may be formed with a partial insert in the tip portion 42 or without any insert in the end effector 13. The insert 44 operating as the electrode is best seen in the exploded view of FIG. 4. Hereafter, when referring to characteristics common to both inserts, the inserts are collectively referred to as "inserts"; and when referring characteristics relating to only the insert operating as an electrode, the insert is referred to as "insert/electrode."

One end of the insert/electrode 44 defines an electrical contact 52 that is ultimately coupled to the power source. In one embodiment, the coupling of the electrical contact 52 to the power source is achieved during the mounting of the end effector 12 on the mounting tip 34. In the instance where the lever member 24 serves as the conductor through the handle 22, the electrical contact 52 engages the mounting tip 34 directly when the end effector 12 is mounted thereto. In an alternative construction, the lever member 24 might not serve as the conductor through the handle 22. In such an instance, the conductor associated with the handle 22 may be in the form of a lead (see FIG. 6) embedded within or mounted along the lever member 24, and terminating in a terminal. The electrical contact 52 would in that instance electrically engage the terminal when the end effector 12 is mounted to the mounting tip 34.

Provided in the tip portions 42 of the end effectors 12, 13 are the cutting portions 50, 51 by which the adenoids are removed. The cutting portions 50, 51 are oriented so that they generally oppose one another. In a preferred embodiment, the cutting portion 50 defined by the insert/electrode 44 is conductive and further defines a blade. The cutting portion 51 in the tip portion 42 of the other end effector 13 is non-conductive and is defined by the body of the end effector 13 so as to form a bearing surface 55, such as an anvil, a pocket, a flat surface or free space, or as an insert in the body, shaped so as to correspond to the shape of the cutting portion 50. In an alternative embodiment, the cutting portion 51 of the other end effector 13 may also be provided as a blade, defined by an insert and be oriented with its edges aligned along a common cutting plane, so that the edges of both cutting portions 50, 51 abut one another when the handles 22 are brought together. Alternatively, the blades of the cutting portions 50, 51 may be slightly off-set relative to one another so as to be able to by-pass each in close proximity and shear the tissue during tissue removal; or the blades of the cutting portions 50, 51 could abut one another at their adjacent cutting edges, but be out of plane, so as to prevent inadvertent contact by the with tissue near the surgical site. In one additional embodiment, the cutting portions 50, 51 could be provided such that they initially engage one another, but that with additional force, the slip or snap passed one another.

Figure 3:
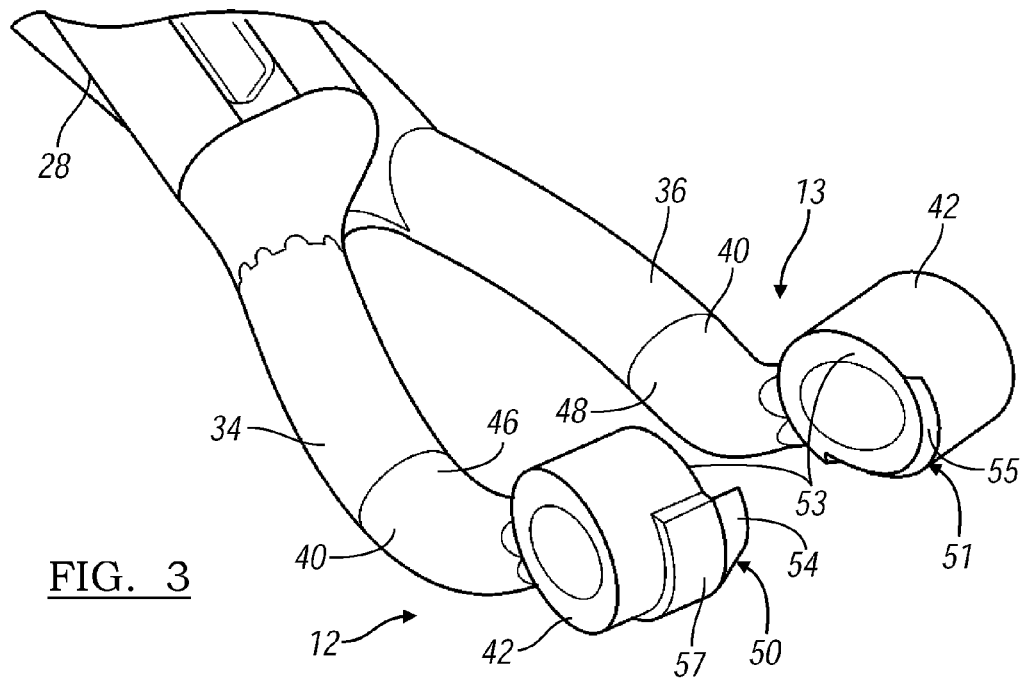
FIG. 3 is a perspective, enlarged view of the end of the cautery forceps seen in FIGS. 2a-2c.
Figure 4:
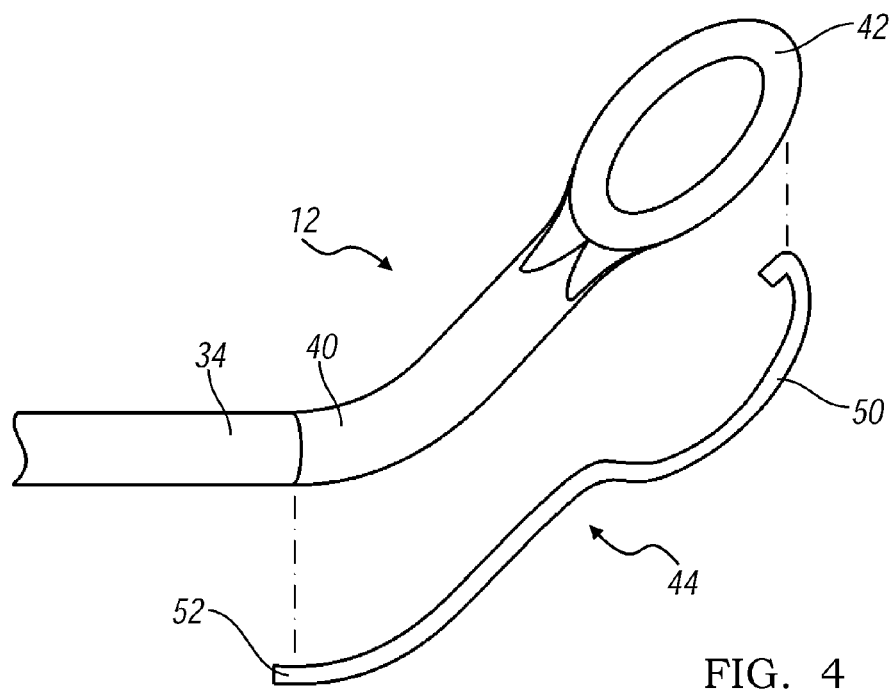
FIG. 4 is an exploded perspective view an end effector as utilized in with the cautery forceps seen in FIG. 2a-2c.

As shown in FIG. 3, the blade of the cutting portion 50 of the insert/electrode 44 is preferably provided with a sharpened edge 54 that interacts with the correspondingly or congruently shaped bearing surface 55 of the cutting portion 51 of the opposing end effector 13, or a sharpened edge thereof, as mentioned above.

In the present embodiment, cutting and cautery of the adenoids are performed by the same component, the cutting portion 50. To this end, adjacent to the blade and sharpened edge 54, the cutting portion 50 is provided with a cautery blade portion 57. The cautery blade portion 57 defines a width extending in a direction away from the sharpened edge 54. Thus, immediately after tissue is dissected from the surgical site by the sharpened edge 54, the cautery blade portion 57 is brought into contact with the dissections site and the remaining tissue cauterized.

The cutting portions 50, 51 may also optionally be provided with a non-stick coating, or other technology, on their surfaces to prevent adhesion and build-up of tissue on the surfaces of the cutting portions 50, 51.

In the above described embodiments, cautery is effectuated by the same component that performs cutting of the adenoid, namely the cutting portion 50. The cautery and cutting functions could, however, be performed by separate components. For example, cutting portion 50 of the insert/electrode 44 may be replaced with separate cutting and cautery blades (non-cutting) in the tip portion 42. The cautery blade, in that instance, would be coupled to the electrical contact 52 and the power source. To sever the adenoids, the separate cutting blade would be provided adjacent to the cautery blade, preferably at a location radially inward on the ovoid ring shaped tip portion 42. Provided in this manner, cautery would be performed as a separate function, but concurrently with removal of the adenoids via the cutting blade.

The insert/electrode 44 of the end effector 12 is preferably insert molded within rigid plastic or another material so that only the cutting portion 50 and the electrical contact 52 are exposed. Insert molded in this manner, inadvertent contact is minimized between the insert/electrode 44 and any tissue that is not the subject of the surgical procedure. As an alternative to insert molding, the insert/electrode 44 could be inserted into previously formed arm and tip portions 40, 42 of the end effector 12.

The insert 45 of the other end effector 13, if provided with an insert, may similarly be insert molded within the end effector 13 or subsequently inserted into the end effector 13 after molding thereof. If no insert is provided in the end effector 13, the inward side of the tip portion 42 is formed in the desired shape of the anvil or blade, depending on the particular configuration of the end effector 13 as described above.

The end effectors 12, 13 are respectively engaged with and mounted to the mounting tips 34, 36 of the lever members 24, 26. In order to mount the end effectors 12, 13 to the handles 22 of the cautery forceps 10, mounting ends 46, 48 of the end effectors 12, 13, are formed so as to matingly engage with the mounting tips 34, 36 of the handles 22. This engagement between the mounting tips 34, 36 of the handles 22 and the mounting ends 44, 46 of the end effectors 12, 13 is preferably a detachable engagement. As such, the engagement may be a press-fit or snap-fit engagement where a portion of the end effector 12, 13 is displaced as it passed over a corresponding portion of the mounting tips 34, 36, and then resiliently snaps back into substantially it original position. Also, a twist/screw/threaded engagement, a keyed engagement, a magnetic engagement or a positive locking or latching construction can be provided. In the illustrated construction of FIG. 2, a snap-fit engagement is provided wherein a portion of the mounting tips 34, 36 is matingly received within a hollow portion of the mounting ends 44, 46.

Alternative Basic Constructions

Figure 6:
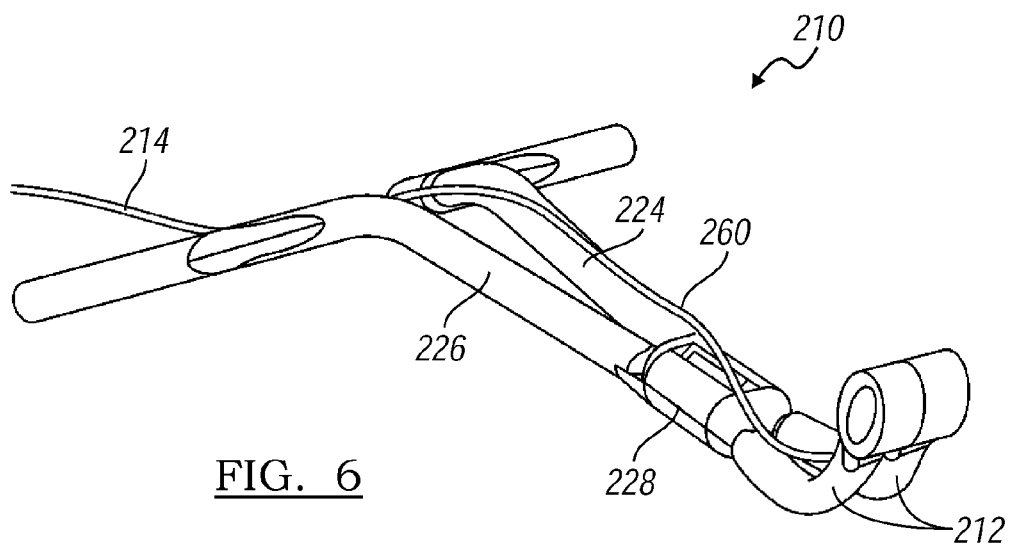
FIG. 6 is a perspective illustration of an alternative embodiment of cautery forceps embodying the principles of the present invention.
Figure 7:
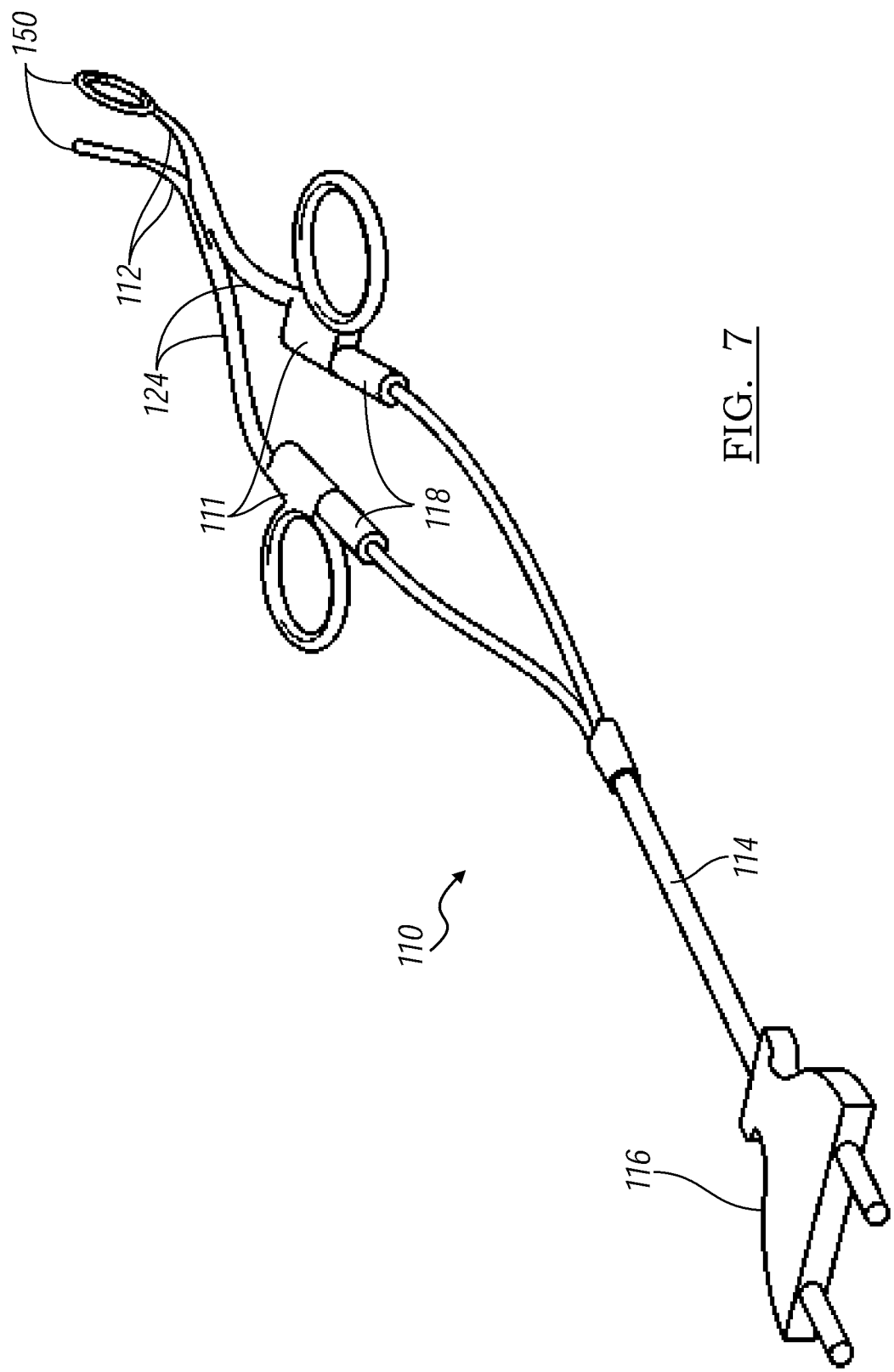
FIG. 7 is a perspective illustration of a further embodiment of cautery forceps embodying the principles of the present invention.

Two alternative constructions of cautery forceps according to the principles of the present invention are shown in FIGS. 6 and 7. In FIG. 6, a monopolar construction is shown wherein current is provided to the conductive end effector via an external lead. In FIG. 7, a bipolar construction is generally illustrated.

Referring to bipolar construction of FIG. 7, the cautery forceps 110 have a construction is similar to that discussed above in connection with the embodiment of FIGS. 2a-3. The bipolar construction differs from the unipolar construction in that both end effectors 112 are conductive and include electrodes for cautery purposes. As a result, each end effector 112 is therefore connected to the power source through its respective the lever member 124, such as with a power cable 114 having terminals 118 for connection to the handles 111 and a plug 116 for connecting to a power source. While they may be the same, the cutting portions 150 of the end effectors 112 also do not need to be identical. They may be appropriately varied as discussed above in connection the end effectors 12, 13. Attention is therefore directed to that section of this description.

In FIG. 6, the means by which the end effectors 212 are connected to the power source is via an external, insulated electrical lead 260. The insulated lead 260 is connected to and supported along the length of the cautery forceps 210. Specifically, the lead 260 is directly connected with the end effectors 212 and does not utilize the lever members 224, 226 of the cautery forceps 210 as a means to electrically couple the power source to the end effectors 212. The lead 260 itself may form a power cable 214 that is connected to the power source, as illustrated, or may be joined with such a cable 214 at a plug connection.

In supporting the leads 260 on the cautery forceps 260, the leads of the cable may be extended through a series of retainers integrally formed on the lever members 224, 226. The retainers may be of any desired shape, e.g. a rectangular shape, an annular ring shape or a C-shape. With a side opening, such as in a C-shaped retainer, the lead 260 may be snapped into the retainer as opposed to being threaded through an opening formed in an enclosed retainer. The retainers therefore may be rigidly or resiliently formed and are sized to positively engage the exterior surface of a lead and retain it positioned therein. The retainers themselves are not illustrated in FIG. 6.

When the cautery forceps 210 are constructed in the manner seen in FIG. 6, the retainers are positioned so as to maintain the lead adjacent to the lever member 224, in an unobtrusive manner, and along the length of the lever member 224. The lead may be position on either side (top and bottom) of the lever member 224

Alternatively, in a bipolar embodiment, each of the two leads may follow the length of its own lever member 224, 226 until engaging the respective end effector 212 mounted thereto. The two leads may alternatively follow one lever member 224, 226 and connect to the end effector 212 associated with the other lever member 224, 226, thereby avoiding the necessity of having the leads 260 cross over one another in the region of the pivot joint 228. In any of the alternative constructions, the retainers 262 should prevent the leads 260 from loosely hanging and should minimize potential interfere by the leads 260 with the surgeon during the surgical procedure.

As an alternative to the scissor-like construction described in the previous embodiments, it should be apparent that the handles could be provided with a tweezers-type construction (a construction where the handles are generally U-shaped or V-shaped and gripped in front of the pivot connection of the lever members and behind the end effectors). The various features of the above discussed embodiments, individually or collectively, could accordingly be applied to the tweezers-type embodiment, or any of the embodiments discussed herein. As a further embodiment, the construction of the cautery forceps could be such that the end effectors are provided as a set of jaws on one end of a shaft, tube or hand piece and operated via manipulation of a trigger mechanism on the other end, as in an endoscope type construction or a pistol grip type of construction.

With all of the above described constructions, the cautery forceps 10, 110, 210 incorporate a reusable handle, after appropriate sterilization. The end effectors themselves may be of a disposable nature or maybe constructed so as to allow for sterilization and reuse. Additionally, the end effectors may be provided, in a variety of sizes and curvatures so as to facilitate their use with different patients and to accommodate a range of different anatomical variations in those patients. As such, the end effectors may be offered individually, either with or without the handles, or maybe offered in a kit format whereby a set of different end effectors, are provided either with or without the handles.

Figure 8:
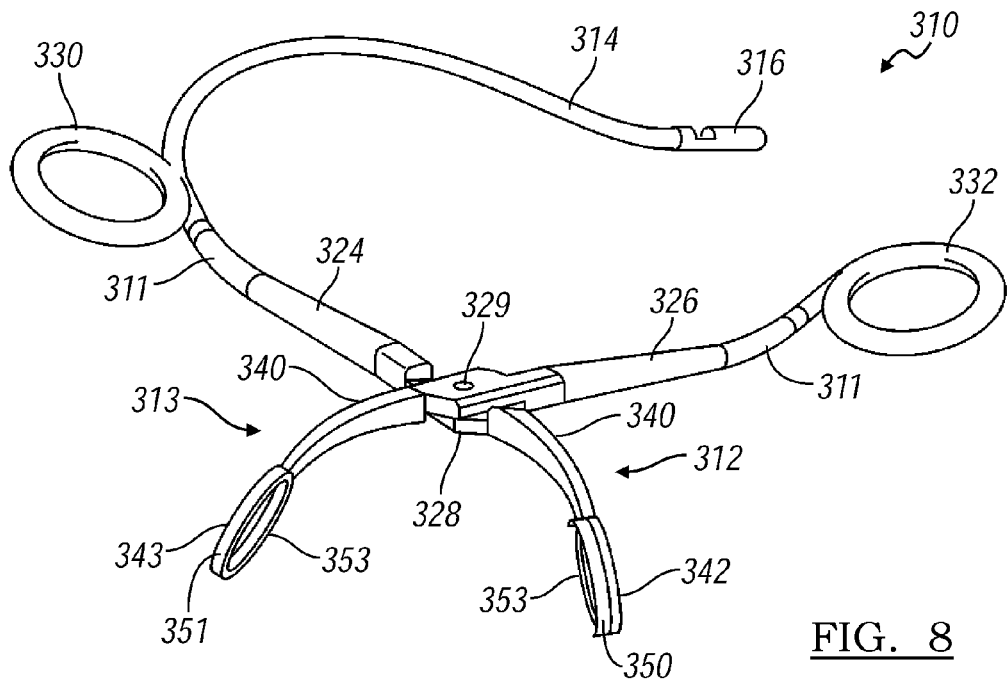
FIG. 8 is an inverted, perspective illustration of an additional embodiment of cautery forceps embodying the principles of the present invention.
Figure 9:
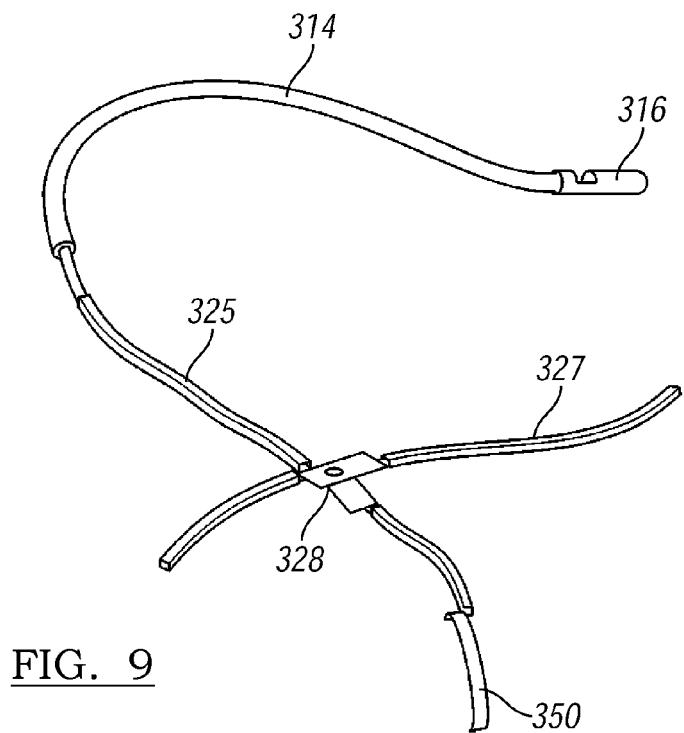
FIG. 9 is a perspective illustration of the embodiment of FIG. 8 showing the underlying frame members of the construction, also in an inverted position.
Figure 10:
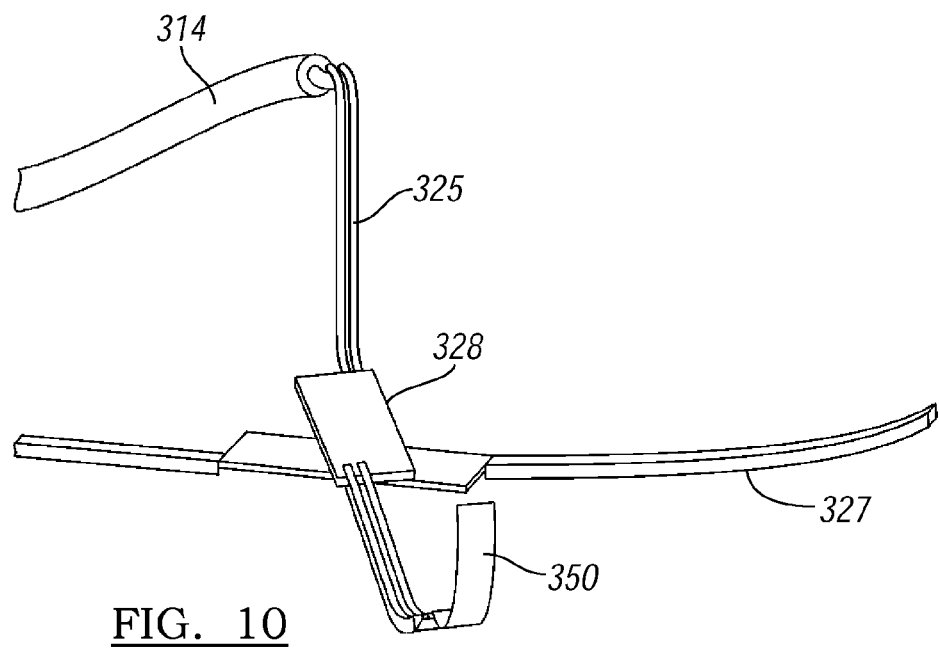
FIG. 10 is an enlarged view of the frame members seen in FIG. 9.
Figure 11:
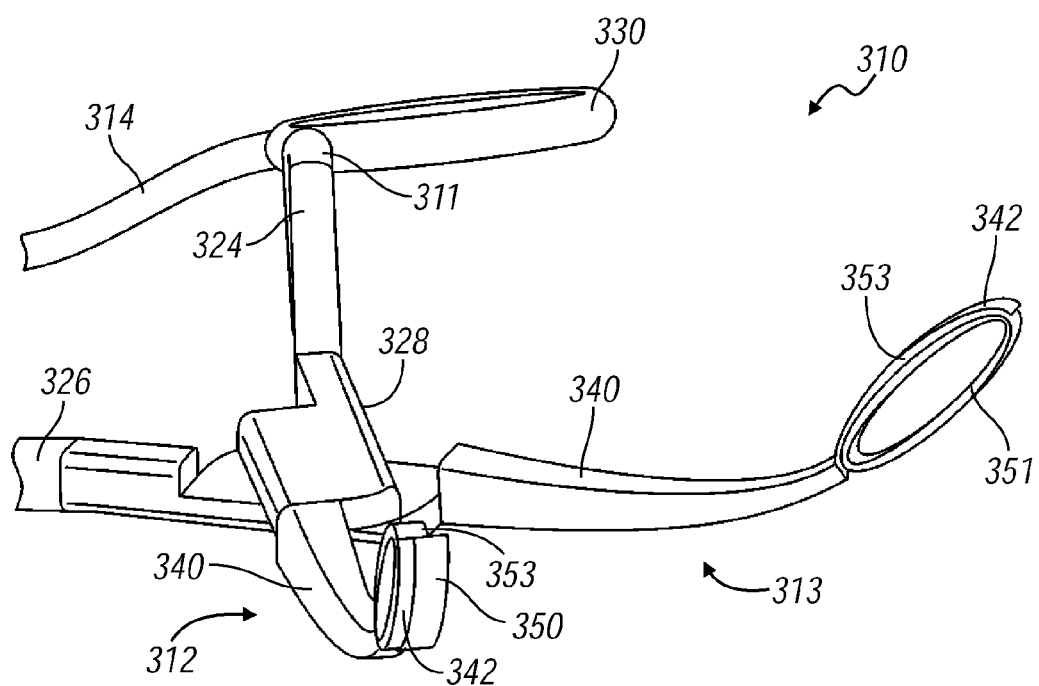
FIG. 11 is an enlarged view of the cautery forceps of FIG. 8, turned over and seen from the opposing side thereof.

Seen in FIGS. 8 and 9 is an additional construction of cautery forceps 310 embodying the principles of the present invention. The cautery forceps 310 of this embodiment are unipolar in their construction, like some of the earlier described embodiments, but do not include detachable end effectors. Rather, the end effectors 312, 313 are non-detachably formed with handles 311 and lever members 324, 326 of the forceps 310. Constructed in this manner, the entire cautery forceps 310 may be of a disposable nature or of a reusable nature, after sterilization, depending on their specific construction.

Like the prior embodiment, the handles 313 of the cautery forceps 310 operate with the two lever members 324, 326 in a traditional, scissors-like construction. The two lever members 324, 326 cross one another at a central pivot joint 328 defined by a pivot axle 329 Each handle 311 includes a finger grip 330, 332 in the form of a ring. By bringing the finger grips 330, 332 together, the end effectors 312, 313 are likewise brought toward one another enabling them to grasp the desired tissue of the patient.

The handles 311, lever members 324, 326 and end effectors 312, 314 are formed by overmolding underlying, rigid frame members 325, 327, which are seen in FIG. 9. The frame members 325, 327 themselves can be constructed of a variety of materials, so long as they impart sufficient strength to the cautery forceps 310 for the surgical procedure to be performed. As such, the materials for the frame members 325, 327 can be a metal material, such as surgical stainless steel, aluminum or another material formed by stamping, cutting, grinding, casting or forging. However, at least one frame member, hereafter the active frame member 325, is constructed from an electrically conductive material so as to be able to transmit electric current through the cautery forceps 310, as further discussed below.

The pivot joint 328 between the frame members 325, 327 is constructed such that it electrically isolates the frame members 325, 327 from one another, particularly if both frame members 325, 327 are formed of metal, and the joint may utilize an insulating bushing.

The overmolding of the frame members 325, 327 electrically isolates them, and in particular the active frame member 325, from the surgeon. While various techniques may be employed to form the overmold, including those discussed above, it is preferred that overmold is formed by insert/injection molding. The exterior surface of the overmold can be textured or smooth, but should facilitate grasping of the handles 311 and finger grips 330, 332, thereby reducing the potential for the cautery forceps 310 to slip in the grasp of the surgeon.

In this embodiment, and alternatively in the prior embodiments, the power cable 314, which is a single strand standard coated RF surgical cable, is permanently attached to one end of the active frame member 325 by soldering, prior to overmolding. The opposing end of the cable 314 includes an accessory plug 316 or a standard three prong surgical plug.

The end effectors 312, 313 have the same general construction and attributes mentioned above, the discussion of which is incorporated by reference, other than being removable, and are principally composed of an arm portions 340 and a tip portion 342, 343, with the latter being formed at the distal end of the arm portions 340. Likewise as previously discussed, the arm portions 340 may be bendable to allow adjustment by the surgeon to accommodate variations in patient anatomy.

As with the prior embodiments, the tip portions 342, 343 are illustrated as having an oval, ring shape to assists in the removal of the adenoids. On the inward and lower side of one of the tip portions 342 is a cutting portion 350. The cutting portion 350 is integrally, and preferably unitarily, formed as an end part of the active frame member 325 and is not fully over molded like other portions of the frame member 325. As such, the cutting portion 350 form an exposed portion of the active frame member 325 and operates as the conductive electrode of the cautery forceps 310. The cutting portion 350 may therefore include a cutting blade with a sharpened edge, optionally provided with a non-stick coating, and a cautery blade having an exposed width for cautery purposes.

The opposing tip portion 343 preferably does not include a cutting portion integrally formed with the frame member 327. Rather, the cutting portion 351 of this tip portion 343 opposes the cutting portion 350 of the active frame member 325 and is preferably formed and defined by the material of the overmold. The cutting portion 351 may define a bearing surface opposing the cutting portion 350 or an edge/blade interacting with the cutting portion 350, as discussed in connection with any of the prior embodiments.

As with the prior embodiments, the upper side of ring shape of the tip portions 342, 343 operate as a mechanism by which the end effectors 312, 314 can grasp the tissue that is being cut, cauterized and removed from the procedure site. While again shown with an ovoid ring shape, the tip portions 342, 343 of the end effectors 312, 313 may have alternative shapes, lengths and widths.

Method of Use

When using the unipolar variations of the cautery forceps, electrical current is delivered to the end effector having the insert/electrode. The cutting portions on the end effectors are then brought to bear against the adenoid tissue that is to be excised. As the adenoid tissue is being removed, current flows from the cutting portion of the insert/electrode, through the adenoid tissue, and out of the patient's body at another electrode that has been attached in a remote location apart from the adenoid tissue. With this passage of current, radio-frequency energy is applied to tissue, heating the water in the local tissues. The heating of the water inherent in the tissue results in a weakening and/or severing of the tissue, allowing mechanical removal and simultaneous cauterizing of removal site.

In the bipolar constructions, the return path for the electric current is defined by the opposing end effector when it is brought near the other end effector. The electrical current will travel through the subject tissue from one end effector to the other. Accordingly, during the cutting and removal of the adenoid tissue, the cutting portions of the end effectors not effectuate removal of the subject tissue, but also cauterizing of the tissue removal site.

To electrically actuate the end effectors of any of the embodiments, a switch may be provided in-line with the power cable. The switch may be in the form of a hand or foot operated switch, or it may be provided as part of the power source. In a further embodiment, the end effectors might be automatically energized when brought into close proximity of one another and therefore not require manipulation of a switch per se. This automatic energizing could be achieved via proximity sensors or limit switches provided as part of the cautery forceps or simply by completing the conductive circuit through the tissue.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

We claim:

1. An electrosurgical instrument for excision of tissue from a patient, the electrosurgical instrument comprising: a handle portion; first and second end effectors configured to excise tissue, the end effectors being connected to and supported by the handle portion for relative movement in a direction generally toward one another; the first end effector including a conductive cutting portion configured to excise tissue from patient, the conductive cutting portion being configured to receive electrical energy from an electrical energy source; the second end effector including an opposing portion, the opposing portion being brought into a position generally opposing the conductive cutting portion during relative movement of the end effectors toward one another, the opposing portion being configured to move to a position where at least part of the opposing portion extends past the conductive cutting portion; the conductive cutting portion defining one lateral extent of the first end effector, the opposing portion defining one lateral extent of the second end effector, wherein the lateral extent of the first and second end effectors is measured in a direction lateral to the direction of movement; and wherein when electrical energy is conducted through the conductive cutting portion, excision and cauterization of the tissue of the patient is facilitated.

2. The electrosurgical instrument of claim 1, wherein the opposing portion is non-conductive, the electrosurgical instrument being a unipolar electrosurgical instrument.

3. The electrosurgical instrument of claim 1, wherein the first and second end effectors include a curved arm portion and a tip, the conductive cutting portion only exposed in the tip.

4. The electrosurgical instrument of claim 3, wherein the tip defines an enlarged lateral width relative to the arm portion and measured in a direction lateral to the direction of movement.

5. The electrosurgical instrument of claim 3, wherein the tip portion is ovoid or ring shaped.

6. The electrosurgical instrument of claim 1, wherein a structural body part of the handle portion is electrically conductive and configured to electrically connect one of the end effectors to the electrical energy source.

7. The electrosurgical instrument of claim 1, wherein the opposing portion is conductive and configured to be electrically coupled to the electrical energy source, the electrosurgical instrument being a bi-polar electrosurgical instrument.

8. The electrosurgical instrument of claim 1, wherein at least part of the opposing portion is offset relative to the conductive cutting portion.

9. The electrosurgical instrument of claim 8, wherein the conductive cutting portion and the opposing portion have complementary shapes to one another.

10. The electrosurgical instrument of claim 1, wherein the end effectors are removably connected to the handle portion in one of press-fit, snap-fit, threaded, keyed, magnetic, positive locking or latching engagement.

11. The electrosurgical instrument of claim 1, wherein end effectors are fixedly connected to the handle portion.

12. The electrosurgical instrument of claim 1, wherein the handle portion is connected to the end effectors by pivotably connected lever members providing the electrosurgical instrument with a scissors construction.

13. The electrosurgical instrument of claim 12, wherein one of the lever members has an electrically conductive body that electrically connects the handle to the conductive cutting portion.

14. The electrosurgical instrument of claim 1, wherein the conductive cutting portion includes a blade defining a leading edge in the direction of movement.

15. The electrosurgical instrument of claim 14, wherein the conductive cutting portion further defines an exposed width portion, the exposed width portion extending in the direction of movement.

16. The electrosurgical instrument of claim 1, wherein the first and second end effectors are disposable.

17. The electrosurgical instrument of claim 1, wherein the conductive cutting portion defines an outboard lateral side of the end effector that is configured to effectuate cautery.

18. An electrosurgical instrument for excision of tissue from a patient, the electrosurgical instrument comprising: opposing first and second end effectors, the first end effector including an exposed electrode defining a cutting portion on a distal end thereof, the cutting portion being configured to effectuate excision of tissue from the patient, the second end effector including an opposing portion located on a distal end thereof and generally opposing the cutting portion, the opposing portion being configured to move to a position where at least part of the opposing portion extends past the cutting portion, the first and second end effectors having generally opposed gripping portions; a handle coupled to the end effectors, the handle configured to cause relative movement of the end effectors in a direction toward each other; the conductive cutting portion defining a lateral extent of the first end effector and the opposing portion defining a lateral extent of the second end effector, the lateral extent of the first and second end effectors being provided on a side of the first and second end effectors that is lateral to the direction of movement, the opposed gripping portions being respectively located on only one side of the conductive cutting portion and the opposing portion; the electrode being directly or indirectly electrically connected to a source of electrosurgical energy; and whereby when electrosurgical energy is applied to the electrode and tissue is located between the electrode and the opposing portion, at least a portion of the tissue is cut and cauterized by the electrode, and can be held between the gripping portions for excision after being cut.

19. The electrosurgical instrument of claim 18, wherein the end effectors are removably connected to the handle in one of press-fit, snap-fit, threaded, keyed, magnetic, positive locking or latching engagement or the end effectors are fixedly connected to the handle.

20. The electrosurgical instrument of claim 18, wherein the cutting portion and opposing portion define congruent surfaces.

21. The electrosurgical instrument of claim 20, wherein the congruent surfaces are aligned with each other when the cutting portion and opposing portion are moved toward each other by the handle.

22. The electrosurgical instrument of claim 18, wherein the source of electrosurgical energy is only connected to the electrode in the first end effector.

23. The electrosurgical instrument of claim 18, wherein each of the end effectors include a tip portion that is oval in shape and the gripping portions are located along one side of tip portion, and the respective conductive cutting and the opposing portions are located along an opposing side of the tip portion.

24. The electrosurgical instrument of claim 18, wherein the electrode defines an outboard lateral side of the end effector that is configured to effectuate cautery.

* * * * *